United States Patent
Corace et al.

[11] Patent Number: 6,036,640
[45] Date of Patent: *Mar. 14, 2000

[54] DEVICE AND METHOD FOR REPOSITIONING THE HEART DURING SURGERY

[75] Inventors: Russell A. Corace, Grand Rapids Township, Mich.; Curtis D. Kinghorn, Lino Lakes, Minn.

[73] Assignee: Medtronic, Inc., Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/637,974

[22] Filed: Apr. 29, 1996

[51] Int. Cl.[7] .................................... A61B 1/313
[52] U.S. Cl. ........................... 600/207; 600/208
[58] Field of Search ................... 600/201, 202, 600/204, 205, 207, 208, 37; 606/192; 601/151, 152, 153

[56] References Cited

U.S. PATENT DOCUMENTS

| | | |
|---|---|---|
| 4,637,377 | 1/1987 | Loop .......................................... 600/37 |
| 4,651,717 | 3/1987 | Jakubczak . |
| 4,984,564 | 1/1991 | Yuen . |
| 5,158,571 | 10/1992 | Picha . |
| 5,163,949 | 11/1992 | Bonutti . |
| 5,211,162 | 5/1993 | Gillen, Jr. et al. . |
| 5,256,139 | 10/1993 | Ghodsian . |
| 5,308,327 | 5/1994 | Heaven et al. ............................. 604/96 |
| 5,318,586 | 6/1994 | Ereren ................................. 600/205 X |
| 5,361,752 | 11/1994 | Moll et al. ............................... 600/205 |
| 5,425,357 | 6/1995 | Moll et al. . |
| 5,439,476 | 8/1995 | Frontzides ........................... 600/207 X |
| 5,520,609 | 5/1996 | Moll et al. ............................... 600/204 |
| 5,613,937 | 3/1997 | Garrison et al. ......................... 600/201 |

FOREIGN PATENT DOCUMENTS

| | | |
|---|---|---|
| 0 573 273 A2 | 8/1993 | European Pat. Off. . |
| 4317762 A1 | 1/1994 | Germany . |
| WO 93/10850 | 6/1993 | WIPO . |
| WO 96/00033 | 1/1996 | WIPO . |

OTHER PUBLICATIONS

PCT/ISA/220—Notification of Transmittal of International Search Report, Jul. 11, 1997.

*Primary Examiner*—Richard J. Apley
*Assistant Examiner*—Denise Pothier
*Attorney, Agent, or Firm*—Foley & Lardner

[57] ABSTRACT

A device for repositioning an organ, such as the heart, during minimally invasive surgical procedures includes a pod having a plurality of inflatable/deflatable pillows on at least an upper surface thereof, each pillow forming a separately sealed chamber. Each chamber may include a separate lumen or supply line in direct communication therewith. Each lumen is in turn connected to a fluid source through either a manually or electrically actuatable valve. The valve associated with each supply line permits fluid to be selectively introduced into or withdrawn from any number of chambers by manipulating the valves to thereby selectively inflate or deflate the selected chambers. Preferably, a pressure sensor is used to monitor the pressure in one or more chambers and means are incorporated to selectively inflate or deflate the chambers in response to the detected pressure.

16 Claims, 5 Drawing Sheets

DEVICE AND METHOD FOR REPOSITIONING THE HEART DURING SURGERY

BACKGROUND OF THE INVENTION

1. Field of the Invention

This invention relates to a device and method for repositioning an organ such as the heart during a surgical procedure and more particularly to a selectively inflated pad positioned immediately adjacent to the heart during minimally invasive surgery.

2. Description of the Prior Art

In open-heart surgery, such as during bypass surgery, a patient's chest cavity is split longitudinally along the sternum and separated to open the chest cavity and expose the heart. With the chest cavity open, the surgeon can easily grasp the heart by hand and manipulate it into the desired position. Unfortunately, opening the chest cavity in the conventional manner is extremely traumatic to the patient, requiring lengthy recuperation.

More recently, minimally invasive surgery (MIS), most usually associated with laparoscopic surgery, has been applied to coronary bypass surgery. One problem associated with this technique is that the surgeon can no longer manipulate the heart by hand resulting in greater difficulty in completing the surgical procedure.

SUMMARY OF THE INVENTION

These and other problems of the prior art are overcome by the provision of an organ elevator and manipulator ideally suited for minimally invasive heart surgery. According to one aspect of the invention, the heart elevator and manipulator includes a pod having a plurality of inflatable/deflatable pillows on at least an upper surface thereof, each pillow forming a separately sealed chamber. Each chamber may include a separate lumen or supply line in direct communication therewith. Each lumen is in turn connected to a fluid source through either a manually or electrically actuatable valve. The valve associated with each supply line permits fluid to be selectively introduced into or withdrawn from any number of chambers by manipulating the valves to thereby selectively inflate or deflate the selected chambers.

According to a further aspect of the invention, a method of manipulating and positioning the heart during minimally invasive heart surgery includes forming an aperture in the patient in the vicinity of a patient—s heart; providing a pod having a plurality of pillows, each pillow forming a sealed chamber in fluid communication with a fluid source; providing a valve between each pillow and the fluid source to selectively inflate or deflate a selected number of pillows; inserting the pod in a rolled state through the trocar; positioning the pod in its unrolled state between the body cavity and the heart; and selectively injecting fluid into at least one of the pillows to thereby inflate the at least one pillow between the heart and body cavity to reposition the heart. The method may also include selectively withdrawing fluid from any of the pillows to further position the heart.

BRIEF DESCRIPTION OF THE DRAWINGS

The invention will now be described with reference to the drawings wherein.

DESCRIPTION OF THE PREFERRED EMBODIMENTS

Figure 1:
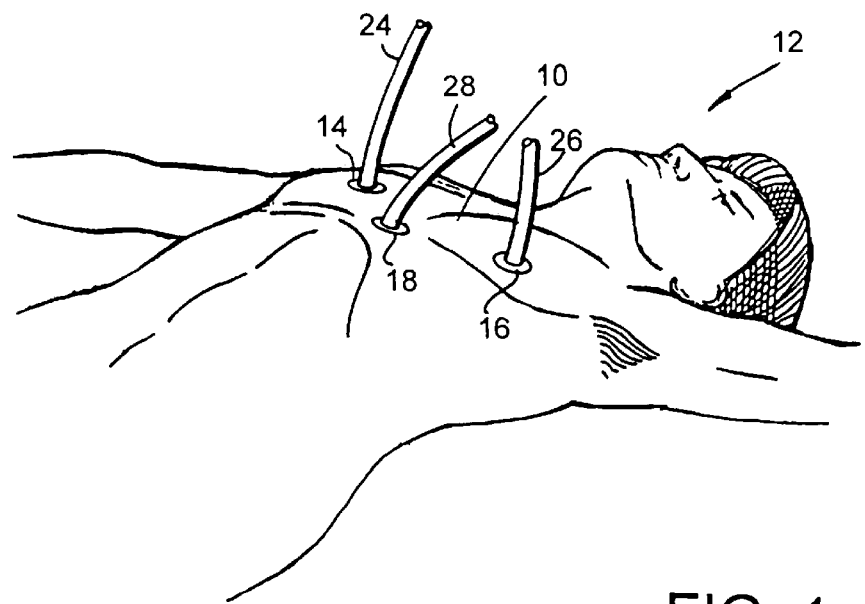
FIG. 1 is a perspective view of a patient during minimally invasive heart surgery.
Figure 4:
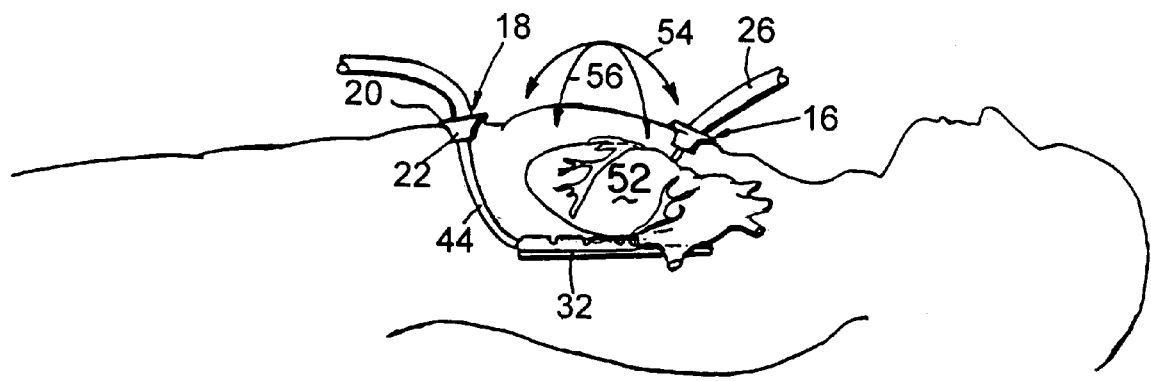
FIG. 4 is a side view of the organ manipulation device in its operative position.

In minimally invasive surgical procedures, such as the minimally invasive heart surgery shown in FIG. 1, multiple small incisions are made in the chest wall for the receipt of surgical instruments. For example, two small incisions are made in the chest wall 10 of a patient 12 at different interstitial rib positions, while a third incision is made just below the sternum. A first trocar 14 is inserted into the first incision at one of the interstices while a second trocar 16 is inserted into the second incision at another of the interstices. Preferably, the first and second incisions are made on opposite sides of the sternum. A third trocar is inserted into the third incision just below the sternum. As best shown in FIG. 4, each trocar is conventional and has a boss 22 depending from a flange 20. The flange 20 is larger in diameter than boss 22, so that when the trocar is installed by pushing the boss through the incision at the interstice between the ribs, the flange will rest on the patient's outer epithelial layer of the external integument. The boss 22 is sufficiently long to fit between the ribs, so that when the trocar is installed, the ribs are spread apart. A central aperture (not shown) extends through each trocar for the reception of surgical instruments, tubes, etc. Once the trocars are installed, conventional devices such as an endoscope, a first surgical instrument, and a secondary instrument, as represented generically by the first cannula 24, second cannula 26, and third cannula 28, are inserted as needed into the central apertures of the several trocars.

Figure 2:
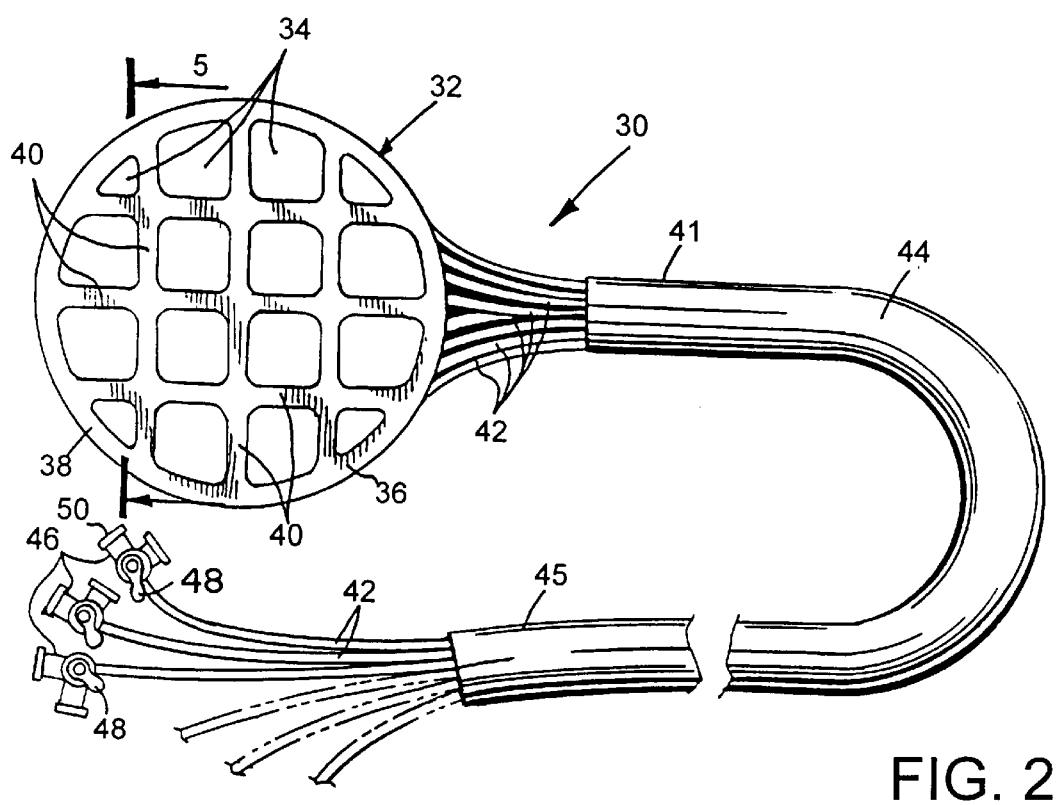
FIG. 2 is a top plan view of the organ manipulation device according to the present invention.
Figure 3:
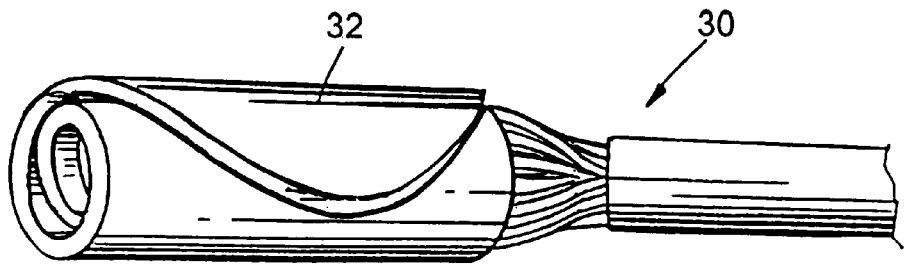
FIG. 3 is a partial, perspective view of the organ manipulation device with the pod in a collapsed, rolled-up state.

Referring now to FIG. 2, a heart elevator and manipulator 30 for use in minimally invasive surgery comprises a pod 32 having a plurality of separately inflatable/deflatable pillows 34 spaced over at least the upper surface 36 of pod 32. The pod is preferably formed of two separate polymeric layers and sealed at the outer peripheral edge 38 and also sealed along partitions 40 to form the several individual pillows 34. The layers may be sealed together through any well-known technique such as heat-sealing or ultrasonic welding. The pod is sufficiently flexible to permit it to be rolled up as shown in FIG. 3. Each pillow 34 forms a separately sealed chamber which is selectively inflatable/deflatable independent of any other pillow. The chamber of each pillow is in fluid communication with a fluid supply line or lumen 42 extending therefrom. Preferably, the several lumens 42 extend from the pod 32 closely adjacent one another and are received in the distal end 41 of a conventional cannula 44. The lumens extend through the proximal end 45 of the cannula 44 and terminate at a stop-cock valve 46. Valve 46 is a well-known valve having a manual actuator 48 to open or close fluid communication between the lumen to which it is attached and a conduit 50. The conduit 50 has an internal bore sized to receive a common syringe (not shown) or other conventional fluid supply source. The valve associated with each supply line permits fluid to be selectively introduced into or withdrawn from any number of selected chambers by manipulating the valves and syringes to thereby selectively inflate or deflate the selected pillow chambers.

In use, after the trocars have been installed, pod 32 is initially in a rolled, collapsed state as shown in FIG. 3. In this position, the rolled pod diameter is smaller than the trocar central opening so that the pod is then inserted through trocar 18 along with a portion of cannula 44 until the pod is fully received in the body cavity. The elasticity of the pod will naturally cause the pod to unroll as it clears trocar 18 to an open state as shown in FIGS. 2 and 4. Once the pod is unrolled, it is positioned adjacent to the heart, preferably beneath the heart. When it is necessary to manipulate or reposition the heart, saline solution, air, or some other acceptable fluid or gas is injected from the fluid supply through one or a plurality of selected valves 46 to selectively fill one or more of the corresponding pillows 34. The pillows can be partially or completely filled to create the desired manipulation of the heart. Valves 36 are initially closed and must be opened by manipulating actuator 48 before injecting the saline solution.

As the saline solution is injected into one or more selected pillows, the pillows 34 begin to expand between the body cavity and heart 52 to position the heart as desired. By selecting the appropriate pillows, the heart 52 can be simultaneously rotated about two orthogonal axes as shown by arrows 54, 56 in FIG. 4. Once a sufficient amount of saline solution is injected into the selected pillow(s), the valves are again closed to prevent saline leakage. Thus, hydraulic pressure from the saline solution in the selected pillows and lumens will keep the heart in its new position until the valves are opened and the syringes are manipulated. Once the surgery is completed or near completion, the pod 32 can be withdrawn by grasping lumens 42 and pulling pod 32 out through the trocar. Pod 32 is sufficiently flexible to permit its withdrawal through the trocar. The rounded outer perimeter 38 of the pod eases the withdrawal through the trocar.

An alternate method of inserting and positioning the pod 32 in a position to manipulate the heart includes rolling the pod sufficiently tight to telescopically fit within cannula 44. The cannula 44 and pod 32 are then inserted as a unit through the trocar until the unit is positioned between the body cavity and the heart 52. The lumens 42 and cannula 44 are then grasped while sliding the cannula with respect to the lumens back through the trocar until pod 32 is completely exposed. Pod 32 will naturally unroll to the open state. If necessary, saline solution can be injected into selected pillows to help the pod unroll.

Figure 5:
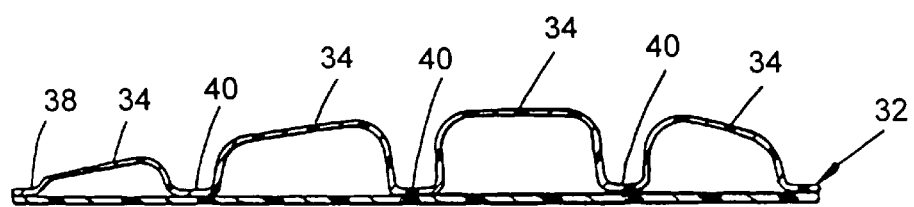
FIG. 5 is a partial, sectional view of the pod of the manipulation device taken along lines 5—5 of FIG. 2.
Figure 6:
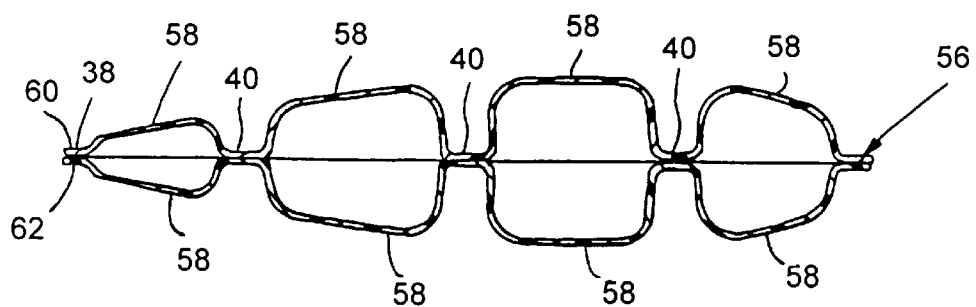
FIG. 6 is a partial, sectional view of the pod similar to FIG. 5, showing a second embodiment of the pod.

As seen in FIG. 5, the pillows of the first embodiment are selectively inflated to varying levels to provide extensive control to the surgeon in repositioning or manipulating the heart. In this embodiment, the pillows 34 are adapted to expand upwardly from the upper surface 36. FIG. 6 shows a second embodiment of the pod 56 in which the pillows 58 are adapted to expand from both the top and bottom surfaces 60, 62, respectively, of the pod 56. In addition to varying the inflation level of the pillows, the size of the pillows can be varied so that additional control in manipulating the balloon is achieved.

The pod 32 is shown in FIG. 2 having a generally circular configuration. However, it is within the scope of the invention for pod 32 to have other configurations including, but not limited to, square, rectangular, oval, crescent shaped and "U" shaped. In the embodiments having a crescent or "U" shaped configuration, the pod 32 may fit around anatomical features and thereby allow the most efficient positioning of the pod 32. In some cases, the use of the crescent of "U" shaped configuration will allow a pod 32 to be used where other shapes could not be accommodated.

Further, it is within the scope of the invention for pillows 34 to have varying heights to conform to certain anatomical areas of the heart and to allow certain areas of the heart to be moved more than others by contact with specific pillows 34. For example, in addition to the embodiments shown, pillows 34 could be selectively inflatable in decreasing heights across the face of pod 32. Alternately, pillows 34 could be selectively inflatable with a maximum height around the peripheral edge 38 of pod 32 and a minimum height near the center of pod 32. Conversely, pillows 34 could be selectively inflatable with a minimum height around the peripheral edge 38 of pod 32 and a maximum height near the center of pod 32.

Figure 7:
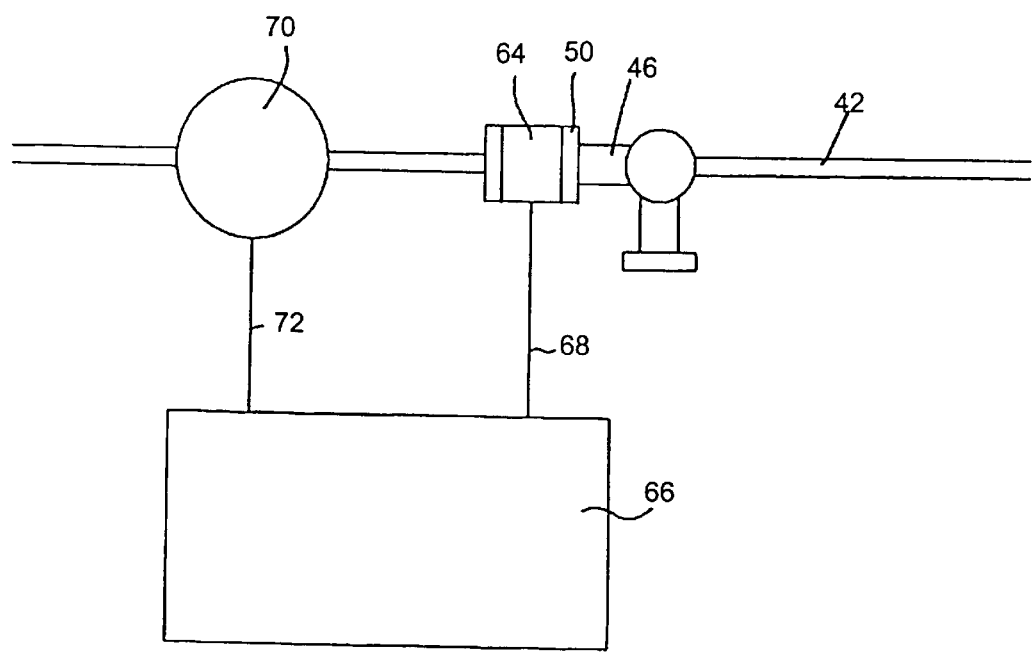
FIG. 7 is a schematic view of a pressure sensor incorporated into the organ manipulation device according to the invention.

In an additional embodiment of the invention seen in FIG. 7, a pressure sensor 64 is attached to at least one lumen 42. In one embodiment, pressure sensor 64 is attached to lumen 42 at conduit 50 so as not to interfere with the presentation of pressurized fluid to lumen 42. Pressure sensor 64 may also be placed within a pillow 34 or near a pillow 34 along lumen 42 on pod 32.

Pressure sensor 64 is electronically attached to a microprocessor 66 through line 68. Microprocessor 66 is attached to a pressurized fluid source 70 through line 72. Pressurized fluid source 70, in one embodiment, may be a control valve placed between a source of pressurized fluid and lumen 42 so that the control valve modulates the fluid pressure supplied to lumen 42 in response to commands from microprocessor 66. In an alternate embodiment, pressurized fluid source 70 may be a pump that is modulated by command signals from microprocessor 66 to provide fluid at different pressures to lumen 42.

In operation, the combination of pressure sensor 64, microprocessor 66, and pressurized fluid source 70 combine to maintain a near constant pressure in lumen 42. Without such a system, as the heart beats, it pushes against a pillow 34 and increases the fluid pressure within pillow 34. As the pressure in pillow 34 increases, pillow 34 becomes more rigid. As a result, the beating heart pushes against and away from pillow 34. Therefore, the beating motion of the heart is accentuated.

In use, the system of the combination of pressure sensor 64, microprocessor 66, and pressurized fluid source 70 acts to increase or decrease the pressure in pillow 34 resulting from the beating motion of the heart to maintain a near constant pressure within pillow 34. In this way, as the beating heart pushes against a pillow 34, thereby causing an increase in the pressure in pillow 34, the pressure is sensed by pressure sensor 64 and is communicated to microprocessor 66. Microprocessor 66 detects an increase in pressure in pillow 34 and directs pressurized fluid source 70 to decrease the pressure in pillow 34. This allows pillow 34 to "give" against the push of the beating heart so that the heart does not press against and move away from pod 32.

Conversely, when microprocessor 66 detects that the pressure detected by pressure sensor 64 is decreasing because the beating heart is contracting, microprocessor 66 directs pressurized fluid source 70 to increase the pressure in pillows 34, thereby more fully inflating pillows 34. This keeps the bulk of the heart from moving closer to pod 32. In this way, the beating heart is always in contact with pod 32 and is kept in essentially the same position despite the fact that the heart is moving while beating.

Figure 8:
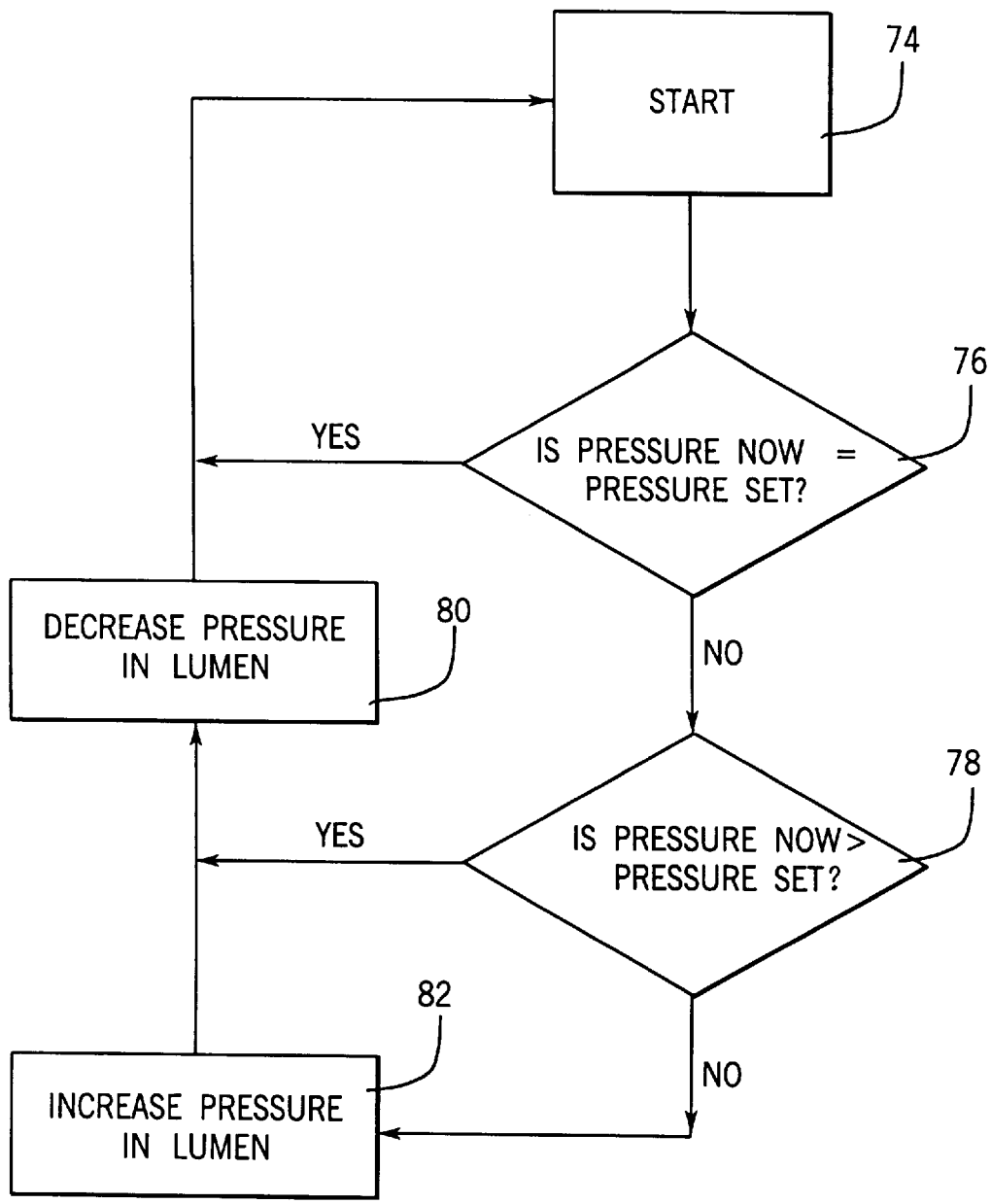
FIG. 8 is a flow chart of one embodiment of a program for controlling the fluid pressure supply to the organ manipulation device.

FIG. 8 shows a flow chart of a possible program to be run by microprocessor 66 to implement the invention described above. In FIG. 8, the pressure detected by pressure sensor 64 is presented to microprocessor 66. The program begins at start block 74. From start block 74, the program moves to decision block 76.

Decision block 76 asks whether the pressure currently sensed by pressure sensor 64 is the same as a set pressure. The set pressure may be an average pressure of the actual pressures sensed by pressure sensor 64 over time or may be a predetermined pressure. If, in decision block 76, the pressure currently sensed is the same as the set pressure, the program loops to the start block 74 to begin the program again.

If, in decision block 76, the pressure currently sensed is not the same as a set pressure, the program passes to decision block 78. Decision block 78 asks whether the pressure currently sensed by pressure sensor 64 is higher than the set pressure. If the answer is yes, the program passes to process block 80 which directs the pressurized fluid source 70 to decrease the fluid pressure sent to pillow 34. The program then passes to start block 74 to begin the program again.

If, in decision block 78, the answer is no, that is, the pressure currently sensed by pressure sensor 64 is not higher than the set pressure, the program passes to process block 82. Process block 82 directs the pressurized fluid source 70 to increase the pressure sent to pillow 34. The program then passes to start block 74 to begin the program again.

The preferred application of the manipulation device according to the invention is for use in minimally invasive heart surgical procedures. However, those skilled in the art will understand that the manipulation device according to the invention can be used in any surgical procedure, minimally invasive or conventional, in which selective control or manipulation of an organ or tissue is desired. For example the manipulation device could be adapted for use in laparoscopic surgical procedures.

While the invention has been described with reference to its preferred embodiment, many modifications may be made to adapt a particular situation or material to the teaching of the invention without departing from its essential teachings. For example, a single pillow or any number of pillows may be formed on the pod. In addition, pillows may be formed on one or both sides of the pod. It will therefore be understood by those skilled in the art that various changes may be made and equivalents may be substituted for elements thereof without departing from the true spirit and scope of the invention as defined by the appended claims.

The embodiments for which an exclusive property or privilege is claimed are defined as follows:

1. A manipulation device for insertion into a body cavity to reposition an organ during a surgical procedure, the manipulation device comprising:

a pod having a first surface for supporting the organ during the surgical procedure and a plurality of selectively inflatable chambers provided in the first surface, the plurality of selectively inflatable chambers being substantially planar and lying generally in a pod plane when in an extended position;

a plurality of fluid conduits each having a proximal end and a distal end, the proximal end of each conduit being fluidly connected to at least one of the plurality of chambers whereby the plurality of chambers are selectively inflatable by means of fluid introduced therein from a fluid supply source by way of the plurality of fluid conduits to tilt the organ; and a second surface opposed to the first surface and the plurality of selectively inflated chambers are provided in both the first and second surfaces and wherein the pod is compressible into a rolled form adapted to be inserted into a body cavity during a surgical procedure, wherein a frame of reference may be defined by a first axis parallel to the pod plane, and a second axis parallel to the pod plane and orthogonal to the first axis, whereby the organ may be simultaneously rotated about the first axis and the second axis by selective inflation of the individual chambers of the plurality of chambers, without repositioning of the pod plane.

2. A manipulation device according to claim 1 wherein each of the plurality of fluid conduits is fluidly connected to a respective one of said plurality of chambers so that each chamber can be independently inflated with fluid supplied by way of the respective fluid conduit.

3. A manipulation device according to claim 2 wherein a valve is provided in each fluid conduit to control the flow of fluid therethrough.

4. A manipulation device according to claim 1 wherein a valve is provided in each fluid conduit to control the flow of fluid therethrough.

5. A manipulation device according to claim 1 wherein the pod comprises first and second layers attached to one another in a manner to define the selectively inflated chambers, the first layer being formed from elastomeric material.

6. A manipulation device according to claim 1 wherein the perimeter of the pod is substantially circular.

7. A manipulation device according to claim 1 and further comprising a pressure sensor fluidly connected to at least one of said plurality of fluid conduits.

8. A manipulation device according to claim 7 and further comprising a microprocessor electrically connected to the fluid supply source and the pressure sensor, the microprocessor being adapted to control the fluid supply source in response to the pressure level detected by the sensor in the fluid conduit.

9. A method of manipulating a body organ during a surgical procedure comprising the steps of:

providing a source of fluid;

forming an aperture in a body;

providing a manipulation device comprising a pod having a first surface and a plurality of selectively inflatable chambers provided in the first surface, wherein the plurality of selectively inflatable chambers are substantially planar lying in a pod plane when in an extended state, and a plurality of fluid conduits each having a proximal end and a distal end, the proximal end of each conduit being fluidly connected to the source of fluid and the distal end of each conduit being fluidly connected to at least one of the plurality of chambers, whereby the plurality of chambers are selectively inflatable with fluid from the by way of the plurality of fluid conduits, the pod being transformable between a retracted state and the extended state;

inserting the pod in the retracted state in the body by way of the aperture; positioning the first surface of the pod inside the body adjacent to the organ to be manipulated; and selectively providing fluid under pressure from the source of fluid to at least one of the chambers to inflate said at least one chamber, whereby inflation of the chamber results in movement of the organ about any two of a multiplicity of axes parallel to the pod plane, without repositioning of the pod plane.

10. A method of manipulating an organ according to claim 9 wherein the aperture is formed pursuant to a minimally invasive surgical procedure and the pod is inserted through the aperture in the retracted state and then transformed to the extended state after the pod is received inside the body.

11. A method according to claim 10 and further comprising the step of providing a valve in at least one of said fluid conduits, the valve being adapted to control the flow of fluid between the source of fluid and the chambers.

12. A method of manipulating an organ according to claim 9 and further comprising the step of providing a pressure sensor in fluid communication with at least one of said plurality of fluid conduits and measuring the fluid pressure present within the at least one fluid conduit.

13. A method according to claim 12 and further comprising the step of selectively venting fluid from at least one of said fluid conduits in response to fluid pressure as detected by the pressure sensor.

14. A method according to claim 12 and further comprising the step of selectively supplying fluid to at least one of said plurality of fluid conduits from the source of fluid in response to fluid pressure as detected by the pressure sensor.

15. A method according to claim 12 wherein the pod in the retracted state is substantially tubular and the pod in the fully extended state is substantially planar.

16. A manipulation device for insertion into a body cavity to reposition an organ during a surgical procedure, the manipulation device comprising:

a pod having a first surface, a second surface opposed to the first surface and a plurality of selectively inflated chambers provided in both of the first and second surfaces, the first surface being adapted to support the organ; and a plurality of fluid conduits each having a proximal end and a distal end, the proximal end of each conduit being fluidly connected to at least one of the plurality of selectively inflated chambers, wherein the plurality of chambers are selectively inflatable by means of fluid introduced therein from a fluid supply source by way of the plurality of fluid conduits to rotate the organ about an axis parallel to a pod plane and wherein the pod is compressible into a rolled form adapted to be inserted into a body cavity during a surgical procedure.

* * * * *

UNITED STATES PATENT AND TRADEMARK OFFICE
CERTIFICATE OF CORRECTION

PATENT NO. : 6,036,640
DATED : March 14, 2000
INVENTOR(S) : Corace et al.

It is certified that error appears in the above-identified patent and that said Letters Patent is hereby corrected as shown below:

Claim 9, column 6, line 58 after "inflatable with fluid from the" please insert --source of fluid--.

Signed and Sealed this

Tenth Day of April, 2001

Attest:

NICHOLAS P. GODICI

Attesting Officer

Acting Director of the United States Patent and Trademark Office